United States Patent
Zhan et al.

(10) Patent No.: US 12,178,885 B2
(45) Date of Patent: Dec. 31, 2024

(54) METHOD FOR MEDIATING TARGETED DELIVERY OF A COMPOSITION TO THE BRAIN OF A SUBJECT IN NEED THEREOF

(71) Applicant: Fudan University, Shanghai (CN)

(72) Inventors: Changyou Zhan, Shanghai (CN); Zui Zhang, Shanghai (CN)

(*) Notice: Subject to any disclaimer, the term of this patent is extended or adjusted under 35 U.S.C. 154(b) by 1056 days.

(21) Appl. No.: 17/251,061

(22) PCT Filed: May 17, 2019

(86) PCT No.: PCT/CN2019/087363
§ 371 (c)(1),
(2) Date: Dec. 10, 2020

(87) PCT Pub. No.: WO2019/237884
PCT Pub. Date: Dec. 19, 2019

(65) Prior Publication Data
US 2021/0252168 A1    Aug. 19, 2021

(30) Foreign Application Priority Data
Jun. 14, 2018 (CN) .......................... 201810626652.4

(51) Int. Cl.
| | |
|---|---|
| A61K 47/64 | (2017.01) |
| A61K 31/65 | (2006.01) |
| A61K 47/69 | (2017.01) |
| A61K 49/00 | (2006.01) |
| A61P 35/00 | (2006.01) |
| C07K 7/06 | (2006.01) |

(52) U.S. Cl.
CPC .......... *A61K 49/0056* (2013.01); *A61K 31/65* (2013.01); *A61K 47/64* (2017.08); *A61K 47/6925* (2017.08); *A61K 49/0093* (2013.01); *A61P 35/00* (2018.01); *C07K 7/06* (2013.01)

(58) Field of Classification Search
CPC .. C07K 7/06; A61K 49/0093; A61K 49/0056; A61K 47/64
See application file for complete search history.

(56) References Cited

U.S. PATENT DOCUMENTS

| 9,790,286 B2 | 10/2017 | Gonzalez | |
| 2013/0344125 A1* | 12/2013 | Govender | .............. A61K 9/127 424/423 |

FOREIGN PATENT DOCUMENTS

| CN | 102151336 A | 8/2011 | |
| CN | 102212116 A | 10/2011 | |
| CN | 103622915 A | 3/2014 | |
| CN | 104558117 A | 4/2015 | |
| CN | 104586765 A * | 5/2015 | |
| CN | 105873615 A * | 8/2016 | ............. A61K 38/00 |
| CN | 106333926 A | 1/2017 | |

OTHER PUBLICATIONS

Sipos et al., Cell Mol. Neurobiol. 30: 405-413, (2010).*
Waqar et al., Hematol. Oncol clin N Am. p. 157-176(2016), only pp. 157, 161,163, and Table 3 are provided.*
Bachmeier C. et al. "A Multifaceted Role for apoE in the Clearance of Beta-Amyloid across the Blood-Brain Barrier", Neurodegener Diseases, 2012, pp. 13-21.
International Search Report, PCT/CN2019/087363, ISA/CN dated Aug. 20, 2019.

* cited by examiner

*Primary Examiner* — Gyan Chandra
(74) *Attorney, Agent, or Firm* — Patshegen IP; Moshe Pinchas

(57) ABSTRACT

A polypeptide modified complex in the pharmaceutical field that can specifically adsorb apolipoproteins in plasma and can mediate a drug across the blood-brain barrier, a target delivery system, and use thereof in preparation of a formulation for diagnosing and treating brain tumors and other brain diseases. The polypeptide fragment (SP) of the amyloid β (relating to one type) is modified shown that the modified delivery system increases uptake the of the amyloid β by vascular endothelial cells after the modified delivery system forms a protein crown with plasma proteins. The modified liposome delivery system delivers a drug to the lesion site more effectively, significantly improving the therapeutic effect of the drug. After the SP adsorbs plasma proteins, a drug may be mediated across the blood-brain barrier and/or targeted to tumor neovascular and tumor cells, and the modified drug and delivery system thereof obtain a better therapeutic effect when treating brain tumors and other diseases in the brain.

13 Claims, 14 Drawing Sheets
Specification includes a Sequence Listing.

c d

|  | sLip | SP-sLip |
|---|---|---|
| $AUC_{0-24}$ (μg/mL·h) | 176 | 153 |
| t1/2 (h) | 10.7 | 10.0 |
| IgG | -3.4 ± 0.3 | -3.7 ± 0.2 |
| IgM | -2.5 ± 0.3 | -2.9 ± 0.4 |

SEQUENCE LISTING

<160> NUMBER OF SEQ ID NOS: 1

<210> SEQ ID NO 1
<211> LENGTH: 11
<212> TYPE: PRT
<213> ORGANISM: Homo sapiens
<220> FEATURE:

```
<221> NAME/KEY: MISC_FEATURE
<222> LOCATION: (11)..(11)
<223> OTHER INFORMATION: amide C terminus

<400> SEQUENCE: 1

Gly Ser Asn Lys Gly Ala Ile Ile Gly Leu Met
1               5                   10
```

METHOD FOR MEDIATING TARGETED DELIVERY OF A COMPOSITION TO THE BRAIN OF A SUBJECT IN NEED THEREOF

The material in the "Sequence Listing" ASCII plain text file titled 350_2_listing_ST25, created on Jul. 5, 2024, size 542 bytes, is hereby incorporated by reference.

CROSS-REFERENCES TO RELATED APPLICATIONS

This application claims priority to and is the National Stage of International Application No. PCT/CN2019/087363, filed on May 17, 2019 and claims priority to Chinese Patent No. CN201810626652.4, filed on Jun. 19, 2018, hereby incorporated by reference in their entirety.

INCORPORATION-BY-REFERENCE OF MATERIALS FILED ON COMPACT DISC

The present application includes a Sequence Listing which has been submitted in ASCII format via EFS-Web and is hereby incorporated by reference in its entirety. Said ASCII copy, created on Dec. 10, 2020, is named INNO1008US_SeqList.txt and is 1, kilo bytes in size.

TECHNICAL FIELD

The invention belongs to the field of pharmacy, which relates to a brain targeted delivery system mediated by amyloid β short peptide (SP), in particular relates to a polypeptide modified compound and targeted delivery system which can specifically adsorb apolipoprotein in plasma and mediate drugs to cross the blood-brain barrier, and application thereof in preparing preparations for diagnosing and treating brain tumors (including brain metastases and primary brain tumors) and other brain diseases.

BACKGROUND OF THE INVENTION

The prior art discloses that central nervous system diseases have become diseases that seriously endanger human health, but the development progress of the research for related new drugs is still very slow. One of the main reasons is that most drug molecules in the drugs are difficult to pass through the blood-brain barrier, and designing drugs or drug delivery systems that can cross the blood-brain barrier is one of the key and difficult points in the field of drug research and development at present. Researches have revealed that the brain-targeted drug delivery system mainly uses receptor-mediated way to cross the blood-brain barrier into the brain, but the current drug design mostly focuses on the binding efficiency of brain-targeted molecules and related receptors on the blood-brain barrier, and the influence of body fluid components is often ignored in the process of in vivo delivery of the drug delivery system. For example, combining plasma proteins to form protein corona can greatly affect the targeting and in vivo circulation time of the drug delivery system, which leads to poor targeting efficiency in vivo of the brain-targeted drug delivery system designed in vitro. How to design brain-targeted drug delivery system from a brand-new perspective, accurately regulate its interaction with related proteins or cells in the process of in vivo delivery, including adsorption and dissociation of plasma proteins, phagocytosis of other cells, protein degradation, immune response, etc., and play a more effective targeting function, is a hot research topic in the current industry.

Based on the current situation of the prior art, the inventor of the present application intends to provide a brain targeted delivery system mediated by amyloid β short peptide (hereinafter referred to as SP), in particular relates to a polypeptide modified compound and targeted delivery system which can specifically adsorb apolipoprotein in plasma and mediate drugs to cross the blood-brain barrier, and application thereof in preparing preparations for diagnosing and treating brain tumors (including brain metastases and primary brain tumors) and other brain diseases. The polypeptide modified targeted delivery system will overcome the defects of traditional targeted nano drugs by regulating the component and biological activity of nano drugs forming protein corona in plasma, and construct an SP- drug complex and SP-modified nano drug delivery system which can cross the blood-brain barrier and target vascular endothelial cells and tumor cells at the same time, thus realizing targeted diagnosis and treatment of brain tumors and drug delivery of other brain diseases.

SUMMARY OF THE INVENTION

The purpose of the present invention is to provide a brain targeted delivery system mediated by amyloid β short peptide (SP), in particular relates to a polypeptide modified compound and targeted delivery system which can specifically adsorb apolipoprotein in plasma and mediate drugs to cross the blood-brain barrier, and application thereof in preparing preparations for diagnosing and treating peripheral tumors, brain tumors and other brain diseases. The polypeptide modified targeted delivery system will overcome the defects of traditional targeted nano drugs by regulating the component and biological activity of nano drugs forming protein corona in plasma, and construct an SP- drug complex and SP-modified nano drug delivery system which can cross the blood-brain barrier and target vascular endothelial cells and tumor cells at the same time, thus realizing targeted diagnosis and treatment of brain tumors (including brain metastases and primary brain tumors) and drug delivery of other brain diseases.

Before explaining the content of the present invention, the terms used herein are defined as follows:

The term "SP" refers to amyloid β short peptide.
The term "PLA" refers to polylactic acid.
The term "PLGA" refers to poly(lactic-co-glycolic acid).
The term "PCL" refers to polycaprolactone.
The sequence (from N to C) of the SP polypeptide of the present invention is $NH_2$-GSNKGAIIGLM-$CONH_2$ (SEQ ID No: 1).

The first aspect of the present invention provides the use of amyloid β short peptide in preparing the preparation for mediating drug molecules, fluorescent probes or delivery systems to target brain tumors and/or focus of other brain diseases, wherein the amyloid β short peptide is amyloid β short peptide that can specifically adsorb apolipoprotein in plasma; preferably, said brain tumor is brain metastatic tumor and/or primary brain tumor.

The use according to the first aspect of the present invention, wherein the amyloid β short peptide is linked to imaging substance X by covalent bond to prepare SP-X, which is used for tracing of brain tumors and focus of other brain diseases;

preferably, in said SP-X, X is a fluorescent molecule Fluorescein or a near-infrared dye molecule Cy5, Cy5.5, Cy7, IR820, ICG, DiR, DiD, DiI;
more preferably, said brain tumor is brain metastatic tumor and/or primary brain tumor.

The use according to the first aspect of the present invention, wherein, the amyloid β short peptide is linked to antitumor drug Y by covalent bond to prepare SP-Y, which is used in targeted intervention of brain tumors and focus of other brain diseases;
preferably, in said SP-Y, Y is gefitinib, icotinib, anlotinib, crizotinib, erlotinib, osimertinib, alectinib, paclitaxel, docetaxel, cabazitaxel, adriamycin, epirubicin, camptothecin, hydroxycamptothecin, 9-nitrocellulose camptothecine or vincristine small molecule antitumor drugs; and/or
in said SP-Y, Y is p53 activating peptide or polypeptide toxin polypeptide antitumor drug;
more preferably, said brain tumor is brain metastatic tumor and/or primary brain tumor.

The use according to the first aspect of the present invention, wherein, the amyloid β short peptide is linked to polyethylene glycol-Z by covalent bond to prepare SP-polyethylene glycol-Z, which is used to prepare nanometer delivery system;
preferably, in said SP-polyethylene glycol-Z, Z is phospholipid, polylactic acid, lactic-co-glycolic acid or polycaprolactone; and/or
preferably, the nano delivery system is selected from one or more of the following: liposome delivery system, micelle delivery system, nano-disc delivery system, and polymer nanoparticle delivery system;
more preferably, the SP-polyethylene glycol-phospholipid is used for preparing the liposome delivery system, the micelle delivery system or the nano-disc delivery system; and/or the SP-polyethylene glycol-polylactic acid, SP-polyethylene glycol- lactic-co-glycolic acid, SP-polyethylene glycol-polycaprolactone are used to prepare the micellar delivery system and the polymer nanoparticle delivery system;
further preferably, the liposome delivery system, the micellar delivery system, the nano-disc delivery system or the polymer nano-particle delivery system is used for encapsulating diagnostic molecules to trace brain tumors or focus of other brain diseases; preferably, the diagnostic molecules encapsulated in the delivery system is 5-carboxyfluorescein 5-FAM or near-infrared dye Cy5, Cy5.5, Cy7, IR820, ICG, DiR, DiD, DiI; and/or
the nanoparticle delivery system, the liposome delivery system, the micelle delivery system, the polymer nanoparticle delivery system or the nano-disc delivery system is used for encapsulating antitumor drugs for targeted intervention of brain tumors and focus of other brain diseases; preferably, the drug encapsulated in the delivery system is gefitinib, icotinib, anlotinib, crizotinib, erlotinib, osimertinib, alectinib, paclitaxel, docetaxel, cabazitaxel, adriamycin, epirubicin, camptothecin, hydroxycamptothecin, 9-nitrocellulose camptothecine, vincristine, p53 activating peptide or polypeptide toxin;
even more preferably, said brain tumor is brain metastatic tumor and/or primary brain tumor.

The second aspect of the present invention provides an amyloid β short peptide for preparing the preparation for mediating drug molecules, fluorescent probes or delivery systems to target brain tumors and/or focus of other brain diseases, characterized in that, the amyloid β short peptide is amyloid β short peptide that can specifically adsorb apolipoprotein in plasma; preferably, said brain tumor is brain metastatic tumor and/or primary brain tumor.

The third aspect of the present invention provides a tracer molecule for brain tumors and focus of other brain diseases, said tracer molecule is SP-X, which is prepared by linking the amyloid β short peptide of claim 5 with the imaging substance X by covalent bond;
preferably, in said SP-X, X is a fluorescent molecule Fluorescein or a near-infrared dye molecule Cy5, Cy5.5, Cy7, IR820, ICG, DiR, DiD, DiI;
more preferably, said brain tumor is brain metastatic tumor and/or primary brain tumor.

The fourth aspect of the present invention provides a drug for targeted intervention of brain tumors and focus of other brain diseases, said drug is SP-Y, which is prepared by linking the amyloid β short peptide of claim 5 with antitumor drug Y by covalent bond;
preferably, in said SP-Y, Y is gefitinib, icotinib, anlotinib, crizotinib, erlotinib, osimertinib, alectinib, paclitaxel, docetaxel, cabazitaxel, adriamycin, epirubicin, camptothecin, hydroxycamptothecin, 9-nitrocellulose camptothecine or vincristine small molecule antitumor drugs; and/or
in said SP-Y, Y is p53 activating peptide or polypeptide toxin polypeptide antitumor drug;
more preferably, said brain tumor is brain metastatic tumor and/or primary brain tumor.

The fifth aspect of the present invention provides a nano delivery system, said nano delivery system comprises the SP-polyethylene glycol- Z, which is prepared by linking the amyloid β short peptide of the second aspect with polyethylene glycol-Z;
preferably, in said SP-polyethylene glycol-Z, Z is phospholipid, polylactic acid, lactic-co-glycolic acid or polycaprolactone;
more preferably, the nano delivery system is selected from one or more of the following: liposome delivery system, micelle delivery system, nano-disc delivery system, and polymer nanoparticle delivery system;
further preferably, when the SP-polyethylene glycol- Z is SP-polyethylene glycol-phospholipid, said nano delivery system is selected from one or more of the following: liposome delivery system, micelle delivery system, nano-disc delivery system; when the SP-polyethylene glycol- Z is SP-polyethylene glycol-polylactic acid, SP-polyethylene glycol-lactic-co-glycolic acid or SP-polyethylene glycol-polycaprolactone, said nano delivery system is micelle delivery system and/or polymer nanoparticle delivery system;
further preferably, said liposome delivery system, micelle delivery system, nano-disc delivery system or polymer nanoparticle delivery system is used for encapsulating diagnostic molecules to trace brain tumors or focus of other brain diseases; preferably, the diagnostic molecules encapsulated in the delivery system is 5-carboxyfluorescein 5-FAM or near-infrared dye Cy5, Cy5.5, Cy7, IR820, ICG, DiR, DiD, DiI; and/or
further preferably, the nanoparticle delivery system, the liposome delivery system, the micelle delivery system, the polymer nanoparticle delivery system or the nano-disc delivery system is used for encapsulating antitumor drugs for targeted intervention of brain tumors or focus of other brain diseases; preferably, the drug encapsulated in the delivery system is gefitinib, icotinib, anlotinib, crizotinib, erlotinib, osimertinib, alectinib, paclitaxel, docetaxel, cabazitaxel, adriamycin, epirubicin, camptothecin, hydroxycamptothecin, 9-nitrocellulose camptothecine, vincristine, p53 activating peptide or polypeptide toxin;

even more preferably, said brain tumor is brain metastatic tumor and/or primary brain tumor.

The sixth aspect of the present invention provides a method for the preparation of the nano delivery system of the fifth aspect, wherein the method comprises the following steps:

weigh natural phospholipid, cholesterol, methoxy-PEG-DSPE, and SP-polyethylene glycol-Z, model drugs or probe molecules, dissolve in the solvent, form a film, hydrate, pass through the membrane, and remove the free probe molecules or drugs by column chromatography to make the nano delivery system; and/or weigh natural phospholipid, cholesterol, methoxy-PEG-DSPE, and SP-polyethylene glycol-Z to dissolve in the solvent, form a film, hydrate, pass through the membrane, actively encapsulate the probe molecules or drugs, and remove the free probe molecules or drugs by column chromatography to make the nano delivery system.

The seventh aspect of the present invention provides a pharmaceutical composition, the pharmaceutical comprises: 1) the amyloid β short peptide of the second aspect, the tracer molecule of the third aspect, the medicine of the fourth aspect and/or the nano delivery system of the fifth aspect; and 2) pharmaceutically acceptable carrier.

The eighth aspect of the present invention provides a diagnostic preparation, said diagnostic preparation comprises: the amyloid β short peptide of the second aspect, the tracer molecule of the third aspect, the medicine of the fourth aspect and/or the nano delivery system of the fifth aspect.

The ninth aspect of the present invention provides a method for treating brain disease, the method comprises: the amyloid β short peptide of the second aspect, the tracer molecule of the third aspect, the medicine of the fourth aspect and/or the nano delivery system of the fifth aspect are administered to a subject in need thereof;

preferably, the brain disease is brain tumor or other brain disease;

more preferably, said brain tumor is brain metastatic tumor and/or primary brain tumor.

The tenth aspect of the present invention provides a method for diagnosing brain tumor and focus of other brain diseases, the method comprises: the amyloid β short peptide of the second aspect, the tracer molecule of the third aspect, the medicine of the fourth aspect and/or the nano delivery system of the fifth aspect are administered to a subject in need thereof; preferably, said brain tumor is brain metastatic tumor and/or primary brain tumor.

The eleventh aspect of the present invention provides a method for targeted intervention of brain tumor and focus of other brain diseases, the method comprises: the amyloid β short peptide of the second aspect, the tracer molecule of the third aspect, the medicine of the fourth aspect and/or the nano delivery system of the fifth aspect are administered to a subject in need thereof; preferably, said brain tumor is brain metastatic tumor and/or primary brain tumor.

The twelfth aspect of the present invention provides a drug-mediated method, characterized in that, the method comprises: the amyloid β short peptide of the second aspect, the tracer molecule of the third aspect, the medicine of the fourth aspect and/or the nano delivery system of the fifth aspect are administered to a subject in need thereof.

According to the present invention, simulate the clearance mechanism of amyloid β in brain with apolipoprotein as molecular partner and receptor-mediated transport to the periphery, and use the amyloid β as a template to design short peptide (SP) which can specifically bind to the apolipoprotein lipid binding domain. By modifying the short peptide on the surface of liposome, apolipoprotein in plasma can be specifically adsorbed and its biological activity can be maintained in the process of blood circulation in vivo, and then apolipoprotein can be combined with various receptors [including low-density lipoprotein-related protein 1 (LRP-1), Scavenger receptor class b member 1 (srb1) and low-density liposome-related protein 2 (LRP-2)] on blood-brain barrier to mediate liposome transport into brain. The polypeptide modified liposome will overcome the defects of traditional targeted nano drugs by regulating the component and biological activity of nano drugs forming protein corona in plasma, and construct an SP- drug complex and SP-modified nano drug delivery system which can cross the blood-brain barrier and target vascular endothelial cells and tumor cells at the same time, thus realizing targeted diagnosis and treatment of brain tumors and drug delivery of other brain diseases.

In the present invention, SP is covalently modified on polyethylene glycol-distearoyl phosphoethanolamine (PEG-DSPE), polyethylene glycol-polylactic acid (PEG-PLA), polyethylene glycol-lactic-co-glycolic acid (PEG-PLGA), polyethylene glycol-polycaprolactone (PEG-PCL) and other materials, and SP short peptide modified liposome, micelle, nano-disk, nanoparticle and the like delivery system are constructed.

The SP modified nano delivery system can encapsulate anti-tumor drugs such as gefitinib, icotinib, anlotinib, crizotinib, erlotinib, osimertinib, alectinib, paclitaxel, docetaxel, cabazitaxel, adriamycin, epirubicin, camptothecin, hydroxycamptothecin, 9-nitrocellulose camptothecine, vincristine, p53 activating peptide, bee venom peptide, scorpion venom peptide, etc. And it can encapsulate fluorescent substances such as FAM, near infrared dyes Cy5, Cy5.5, Cy7, IR820, ICG, DiR, DiD, DiI, etc.

In the present invention, SP modified drugs or probes include pH sensitive hydrazone bonds formed by reaction of maleimide hydrazide derivatives, involving drugs such as adriamycin, epirubicin, p53 activating peptide and polypeptide toxin; or disulfide bonds formed by reaction of 3-(2-pyridine dimercapto) propionic acid derivatives, involving drugs such as gefitinib, icotinib, anlotinib, crizotinib, erlotinib, osimertinib, alectinib, paclitaxel, docetaxel, cabazitaxel, camptothecin, hydroxycamptothecin, 9-nitrocellulose camptothecine, vincristine, p53 activating peptide, polypeptide toxin; or connects fluorescent probes through stable chemical bonds, involving Fluorescein, Cy5, Cy5.5, Cy7, ICG, IR820.

Furthermore, the invention provides the application of amyloid β short peptide in preparing the preparation for mediating drug molecules, fluorescent probes or delivery systems to target brain tumors (including brain metastases and primary brain tumors) or focus of other brain diseases, wherein the amyloid β short peptide is amyloid β short peptide that can specifically adsorb apolipoprotein in plasma.

The amyloid β short peptide (SP) is linked to imaging substance X by covalent bond to prepare SP-X, which is used for tracing of brain tumors (including brain metastases and primary brain tumors) and focus of other brain diseases;

in said SP-X, X is a fluorescent molecule Fluorescein or a near-infrared dye molecule Cy5, Cy5.5, Cy7, IR820, ICG, DiR, DiD, DiI.

The amyloid β short peptide (SP) is linked to antitumor drug Y by covalent bond to prepare SP-Y, which is used in targeted intervention of brain tumors (including brain metastases and primary brain tumors) and focus of other brain diseases; in said SP-Y, Y is gefitinib, icotinib, anlotinib, crizotinib, erlotinib, osimertinib, alectinib, paclitaxel, docetaxel, cabazitaxel, adriamycin, epirubicin, camptothecin, hydroxycamptothecin, 9-nitrocellulose camptothecine or vincristine small molecule antitumor drugs; in said SP-Y, Y is p53 activating peptide or polypeptide toxin polypeptide antitumor drug.

The amyloid β short peptide (SP) is linked to polyethylene glycol-Z by covalent bond to prepare SP- polyethylene glycol-Z, which is used to prepare nanometer delivery system; in said SP-polyethylene glycol-Z, Z is phospholipid, polylactic acid (PLA), lactic-co-glycolic acid (PLGA) or polycaprolactone (PCL).

The SP-polyethylene glycol-phospholipid of the present invention is used for preparing the liposome delivery system, the micelle delivery system or the nano-disc delivery system.

The SP-polyethylene glycol-polylactic acid, SP-polyethylene glycol- lactic-co-glycolic acid, SP-polyethylene glycol-polycaprolactone of the present invention are used to prepare the micellar delivery system and the polymer nanoparticle delivery system.

The liposome delivery system, the micellar delivery system, the nano-disc delivery system or the polymer nanoparticle delivery system of the present invention is used for encapsulating diagnostic molecules to trace brain tumors (including brain metastases and primary brain tumors) or focus of other brain diseases; the diagnostic molecules encapsulated in the delivery system is 5-carboxyfluorescein 5-FAM or near-infrared dye Cy5, Cy5.5, Cy7, IR820, ICG, DiR, DiD, DiI.

The nanoparticle delivery system, the liposome delivery system, the micelle delivery system, the polymer nanoparticle delivery system or the nano-disc delivery system of the present invention is used for encapsulating antitumor drugs for targeted intervention of brain tumors (including brain metastases and primary brain tumors) or focus of other brain diseases; the encapsulated drug is gefitinib, icotinib, anlotinib, crizotinib, erlotinib, osimertinib, alectinib, paclitaxel, docetaxel, cabazitaxel, adriamycin, epirubicin, camptothecin, hydroxycamptothecin, 9-nitrocellulose camptothecine, vincristine, p53 activating peptide or polypeptide toxin;

More specifically, the invention is realized by the following technical solution:

1. Preparation of SP Modified Liposome Delivery System

SP containing cysteine sulfhydryl and maleimide -PEG-DSPE are reacted in phosphate buffer at PH 7.4. After purification, the product is lyophilized to prepare SP-PEG-DSPE for later use.

Weigh a certain amount of natural phospholipid, cholesterol, methoxy -PEG-DSPE (mPEG-DSPE), with SP-PEG-DSPE, model drugs or probe molecules, dissolve them in solvent, form a film, hydrate, pass through the membrane by liposome extruder, remove the free probe molecules or drugs by column chromatography, and the SP polypeptide modified liposome is prepared. Its particle size and surface potential are characterized by dynamic light scattering particle size analyzer. Or weigh a certain amount of natural phospholipid, cholesterol, methoxy-PEG-DSPE (mPEG-DSPE) and SP-PEG-DSPE, dissolve in solvent, form a film, hydrate, pass through the membrane by liposome extruder, actively encapsulate the probe molecules or drugs, remove free probe molecules or drugs by column chromatography, and the SP polypeptide modified liposome is prepared. Its particle size and surface potential are characterized by dynamic light scattering particle size analyzer.

2. Experiment of the Influence for the Binding Activity of SP Modified Delivery System after Incubating with Plasma to Form Protein Corona After incubate the SP modified delivery system with fresh plasma for a period of time, the binding activity of it to LRP-1 receptor is detected by western blot and radioactive labeling method. The SP modified delivery system which is not incubated with serum and the unmodified SP delivery system are used as negative control.

3. Experiment of the Influence that SP Modification on Uptake of Delivery System by Vascular Endothelial Cell System The uptake of SP modified and unmodified delivery system by vascular endothelial cells (such as bEND.3 cells) are compared before and after serum incubation.

4. Evaluation of the Ability of SP Modified Delivery System to Cross BBB in Normal Mice Normal mice (such as Kunming, C57BL/6, etc.) are injected with fluorescein-loaded delivery system via tail vein, and the accumulation of SP modified and unmodified delivery system in mice brain at different time points are compared.

5. Pharmacokinetics Evaluation of SP Modified Delivery System in Normal Rats

Normal SD rats are injected with fluorescein DiI labeled polypeptide modified and unmodified delivery systems via tail vein. Blood is collected at different time points, plasma is separated, and the content of DiI in plasma is quantitatively detected by fluorescence to evaluate the pharmacokinetics of SP modified delivery system in rats.

6. Evaluation of Immunogenicity of SP Modified Delivery System in Normal Mice

The polypeptide modified and unmodified delivery system containing Lipid A are prepared and injected intraperitoneally into Balb/c mice, once every seven days in four weeks. Blood is collected from the orbit on the seventh day after each injection, and plasma is collected and frozen for later use. ELISA is used to detect the content of IgG and IgM against PEG and SP in the mice at different time points and to evaluate the immunogenicity.

7. Evaluation of Anti-Tumor Effect of SP Modified Delivery System In Vivo

By injecting SP modified delivery system, unmodified polypeptide delivery system, free drug and normal saline into nude mice bearing orthotopic U87 glioma model via tail vein, the anti-tumor effect of SP modified delivery system in vivo is evaluated with the median survival time, apoptosis of tumor tissue and neovascularization density as indicators.

Tests show that the SP mediated drug or drug delivery system targets cells and tissues with high LRP-1 expression, which has the capability of crossing biological membrane barrier, especially the capability of crossing blood-brain barrier (BBB), and can be used for targeted diagnosis and treatment of brain tumors (including brain metastases and primary brain tumors) and other diseases.

Experiments show that SP is modified on the surface of the drug delivery system and combined with apolipoprotein in plasma to form a protein corona and increase the uptake of vascular endothelial cells; SP can mediate drugs across the blood-brain barrier and/or target tumor neovascularization and tumor cells at the same time. The modified drugs and drug delivery system can achieve better therapeutic effects in the treatment of brain tumors (including brain metastases and primary brain tumors) and other diseases in the brain.

Figure 1A:
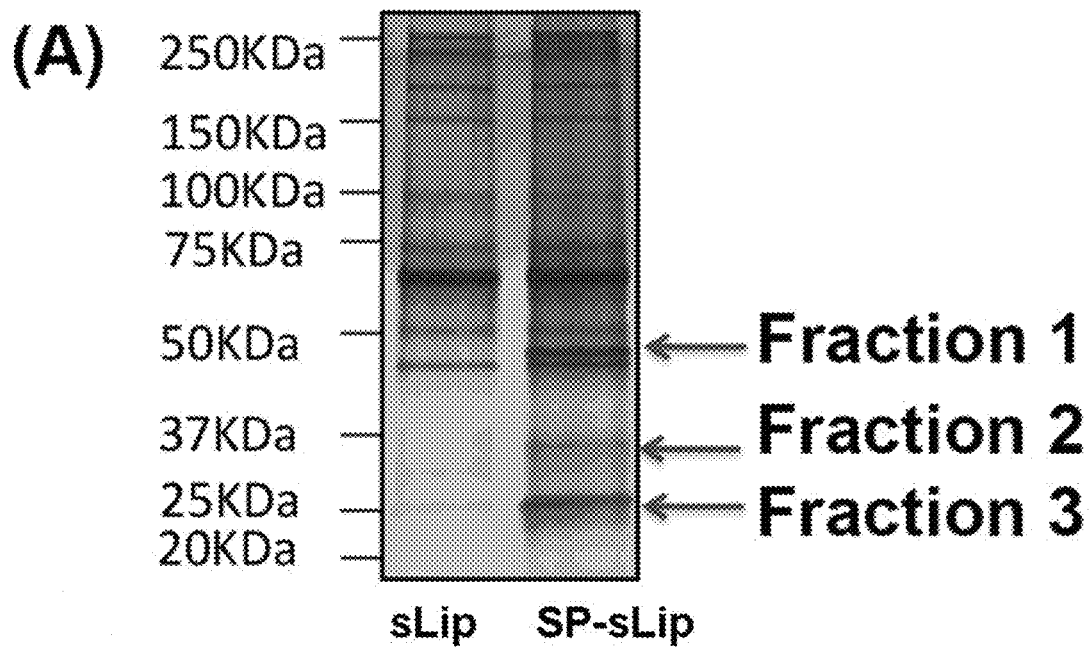
FIG. 1 is the in vitro binding identification of SP modified liposomes and plasma proteins.
Figure 1B:
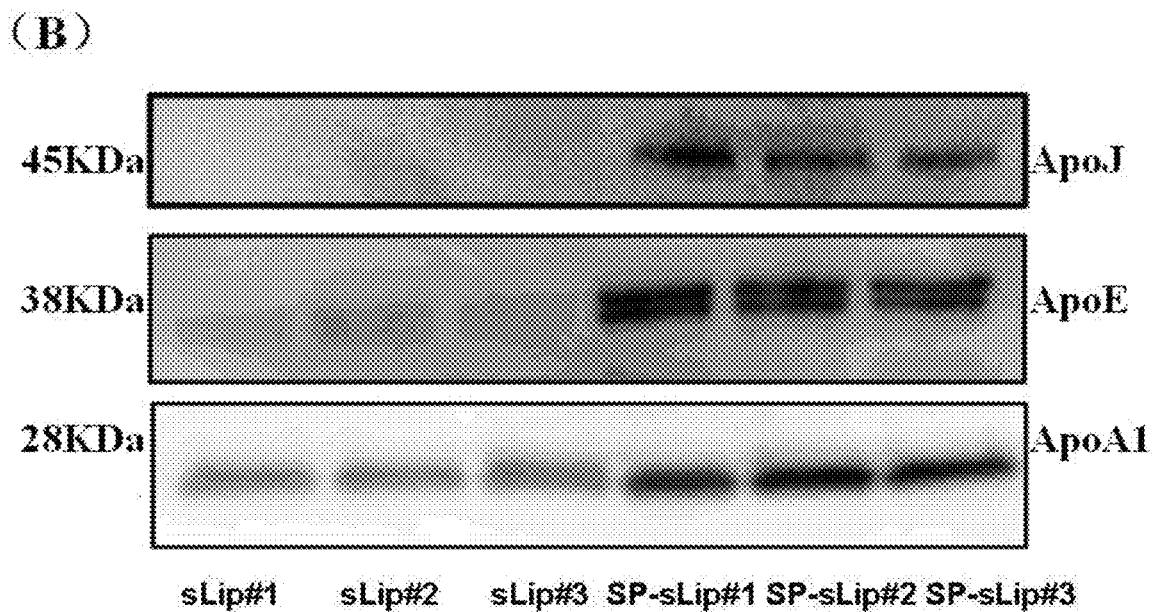
Figure 1C:
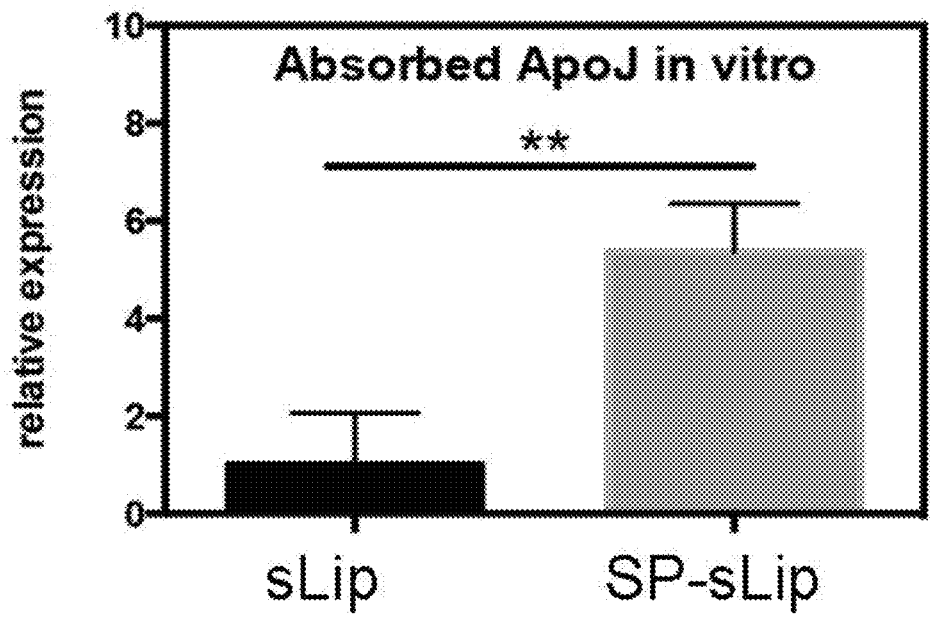
Figure 1D:
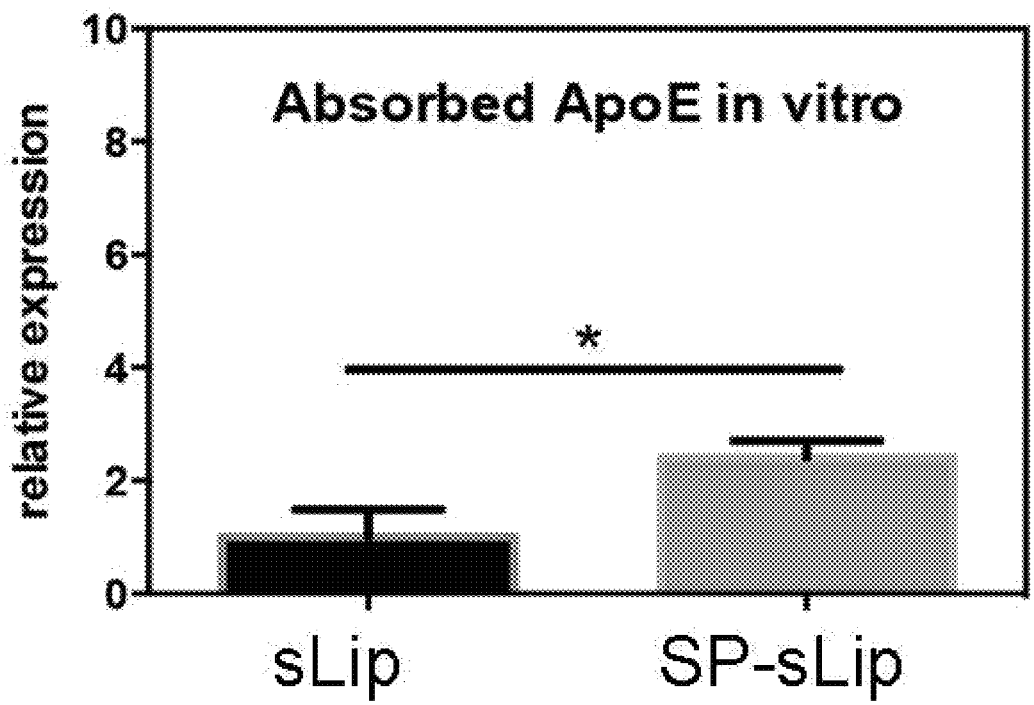
Figure 1E:
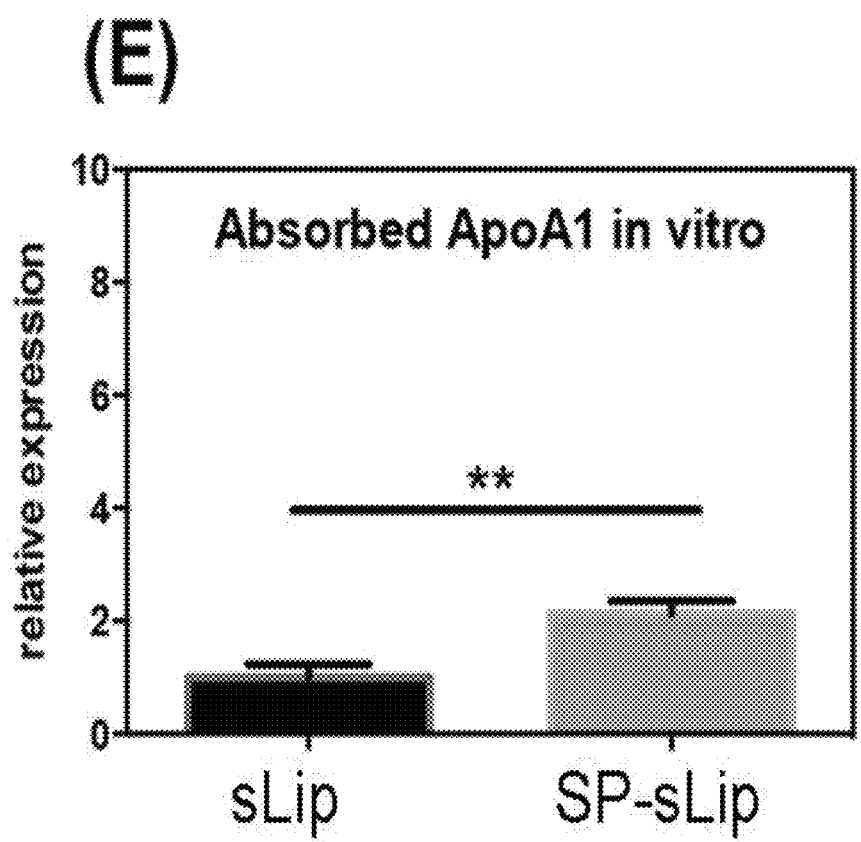

SP was modified on the surface of liposome by chemical coupling to obtain SP-sLip, which was mixed with mouse plasma and incubated at 37° C. for 1 h, and then centrifuged at high speed to obtain liposome precipitate containing protein corona. After Biorad 4%-20% gradient SDS-PAGE separation, the plasma protein components adsorbed by liposomes were analyzed by rapid silver staining (as shown in FIG. 1A). Compared with methoxy polyethylene glycol modified long circulating liposome (sLip), the bands of plasma protein adsorbed by SP-sLip at 45 KDa (band 1), 38 KDa (band 2) and 25 KDa (band 3) increased significantly. The results of LC-MS/MS and western blot (as shown in FIG. 1B) were analyzed on PAGE glue corresponding to the same position in three places, and the three proteins were identified as ApoJ, ApoE and ApoA1 from mice. Western blot semi-quantitative method also confirmed that SP-sLip adsorbed three apolipoproteins significantly more than sLip (as shown in FIG. 1C-E).

FIG. 2 is the identification of the adsorption of plasma functional apolipoprotein by fluorescent labeled sLip and SP-sLip in vivo.

Figure 2A:
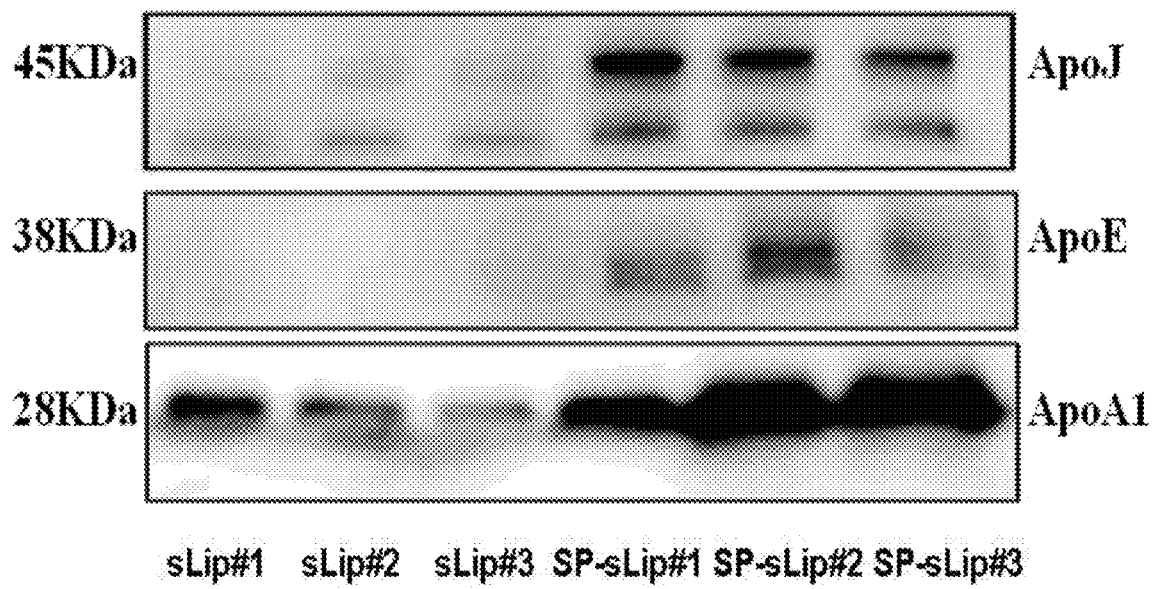
Figure 2B:
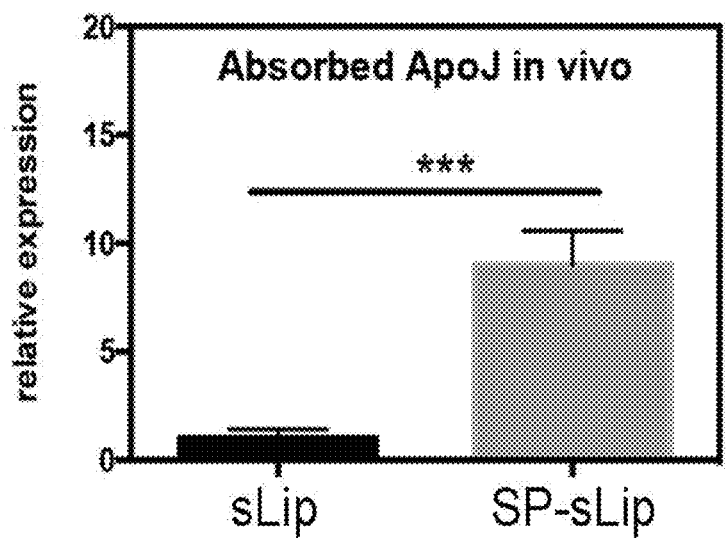
Figure 2C:
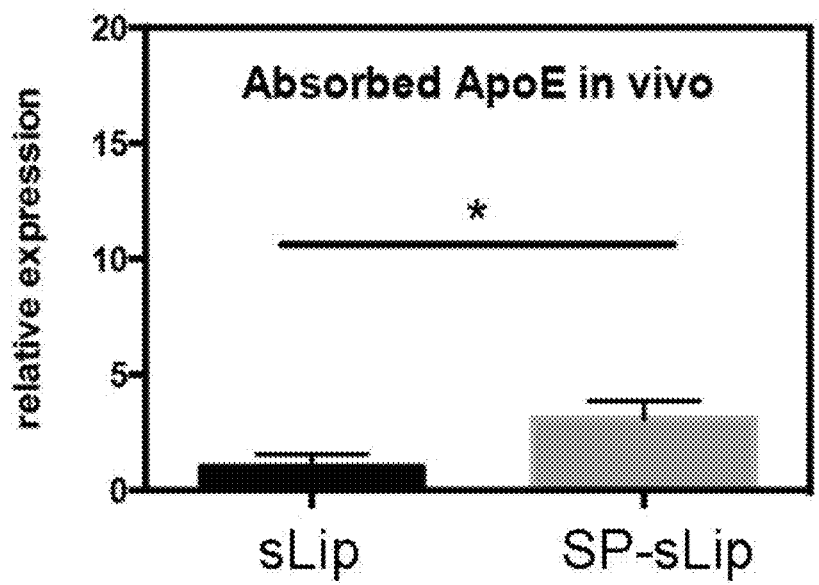
Figure 2D:
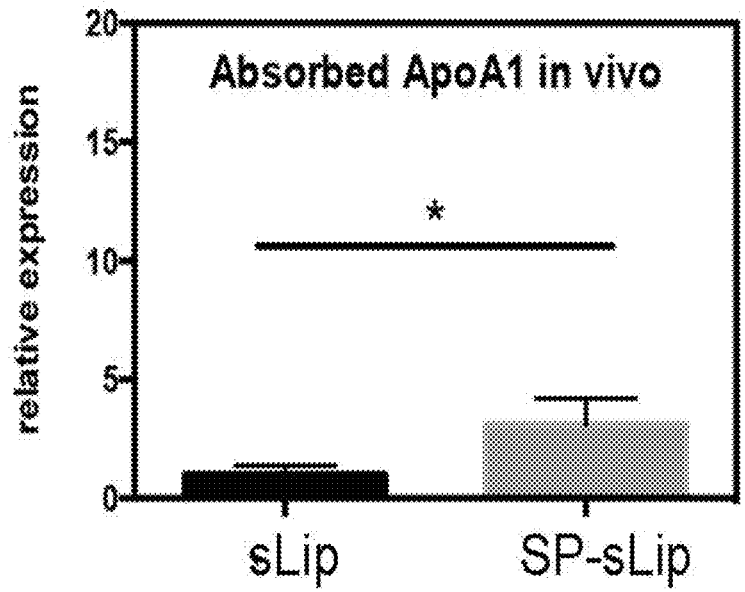

In order to verify that liposomes modified by target small peptides can still adsorb related target proteins after systemic administration in animals, we injected the same amount of DiI fluorescence labeled liposomes into mice via tail vein, and then took the blood 1 h later to separate liposomes containing protein corona in plasma. As shown in FIG. 2A, western blot showed that there were significant differences in the contents of three apolipoproteins (ApoJ, ApoE and ApoA1) adsorbed by liposomes with the same content in mice. This result proves that SP modified liposome (SP-sLip) can quickly and specifically adsorb apolipoproteins in plasma proteins in mice compared with ordinary liposomes. (as shown the semi-quantitative analysis in FIG. 2B-D)

FIG. 3 is the evaluation of binding activity of sLip and SP-sLip to LRP-1 receptor after adsorption of plasma protein.

Figure 3A:
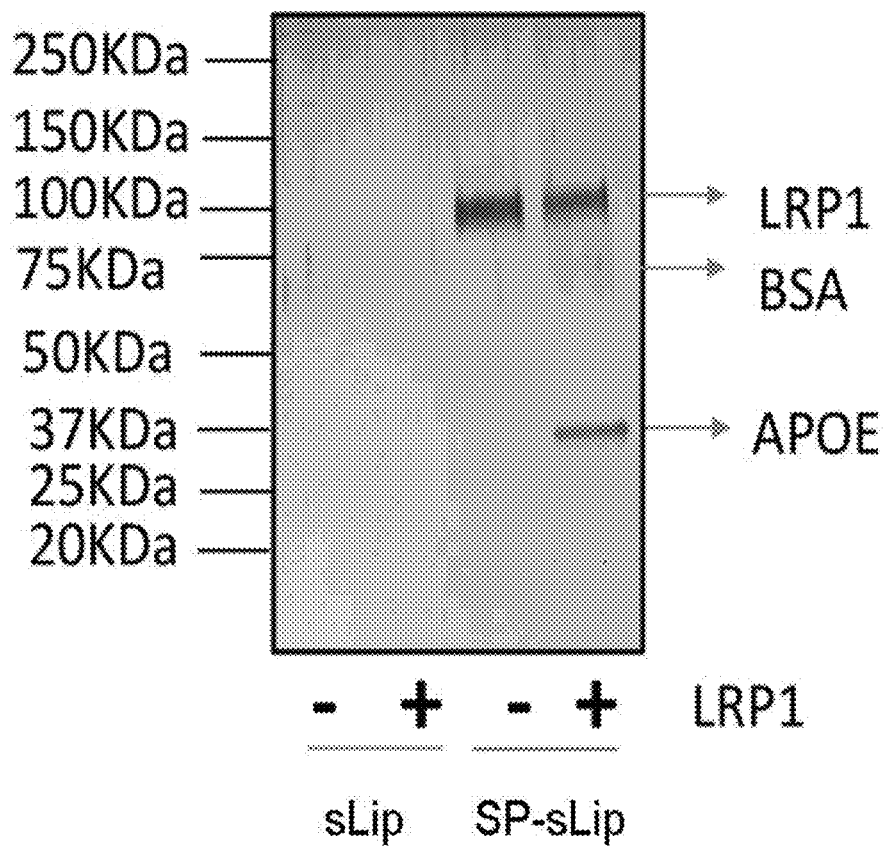
Figure 3B:
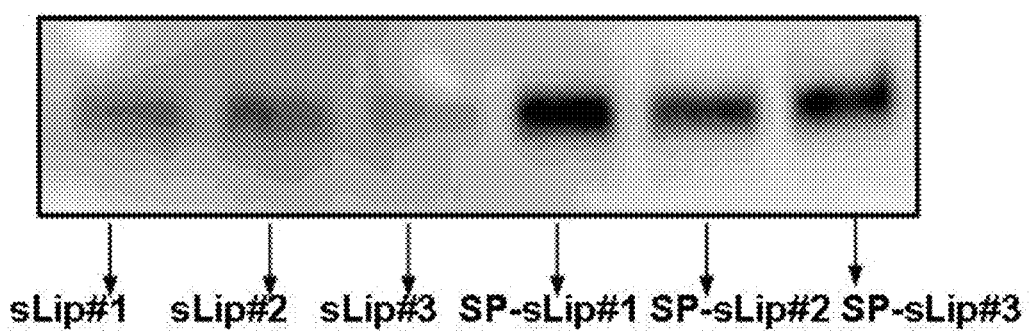
Figure 3C:
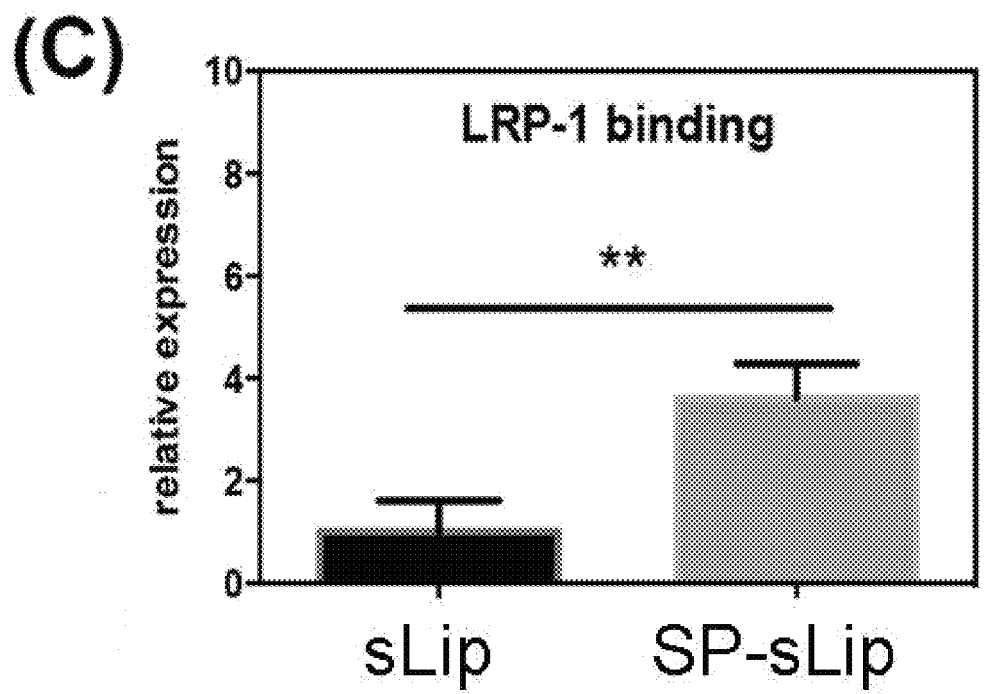
Figure 3D:
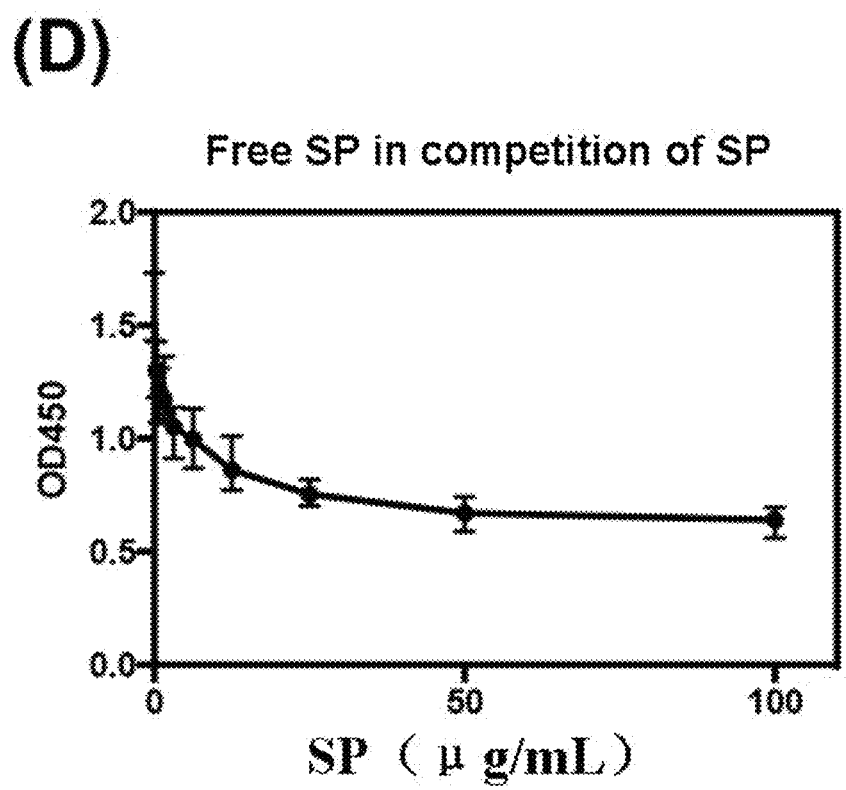
Figure 3E:
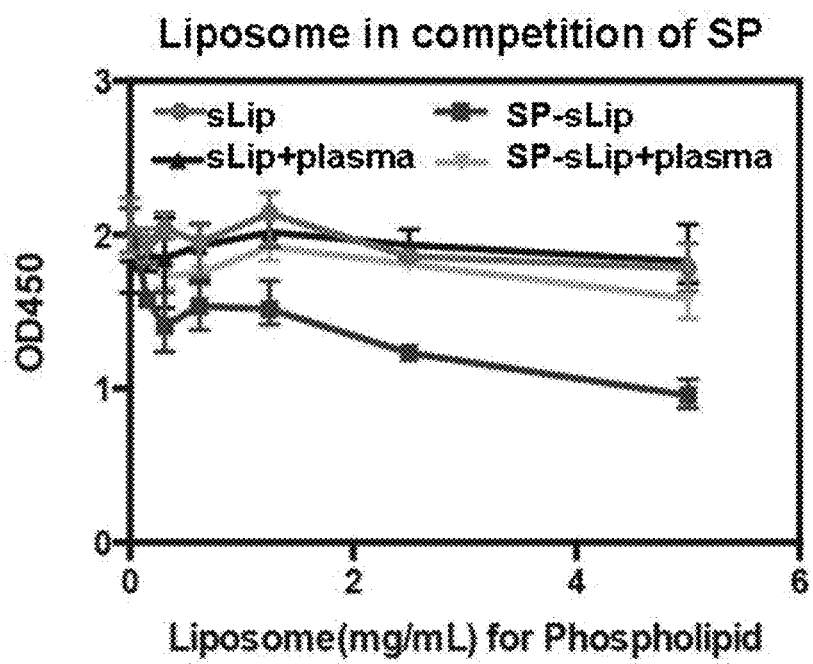

SP modified liposome (SP-sLip) itself can specifically adsorb recombinant protein LRP-1 in solution (as shown in FIG. 3A). We confirmed by western blot that SP-sLip still retains the ability to bind LRP-1 after preincubation with ApoE (as shown in FIG. 3B-C). FIG. 3DE proved by ELISA that both free SP and modified liposome (SP-sLip) can compete for the interaction between SP and antibody fixed on 96-well plate, while SP-sLip losed the ability to compete for antibody binding after plasma incubation, which indicated that the functional domain of SP on the surface of liposome was blocked after binding with plasma proteins such as ApoE. Apolipoprotein, such as ApoE, which can specifically binds to the surface of SP-sLip, has the activity of binding to BBB receptor LRP-1, which has become an effective way to mediate SP-sLip to enter the brain across BBB.

FIG. 4 is the uptake of liposomes by vascular endothelial cells before and after plasma incubation.

Figure 4A:
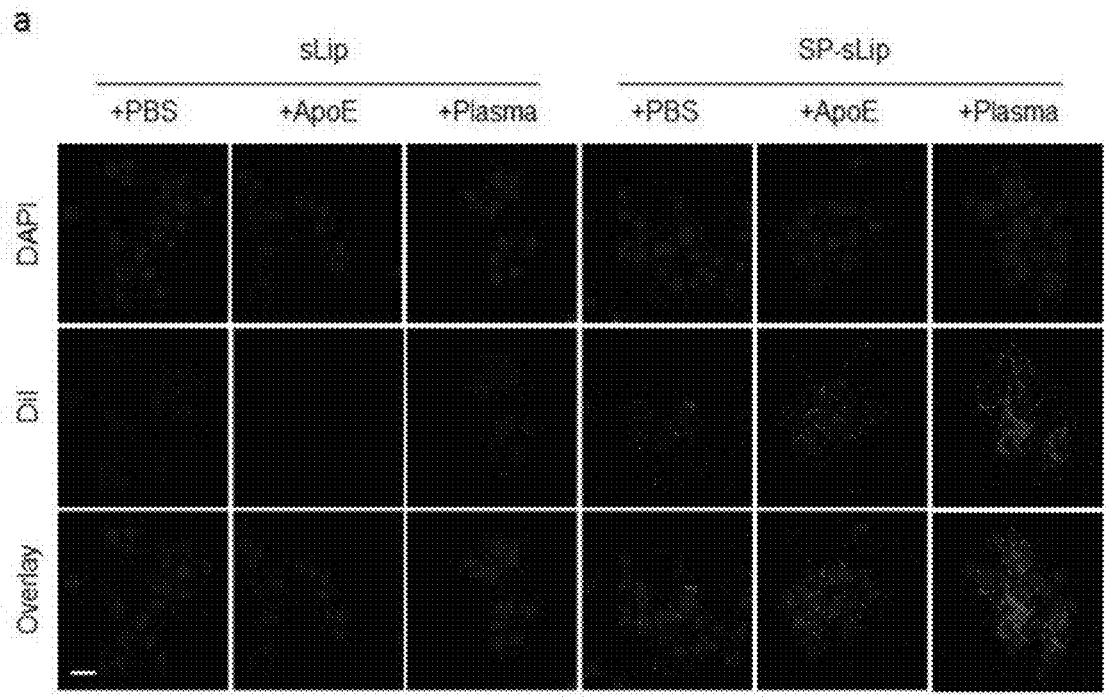
Figure 4B:
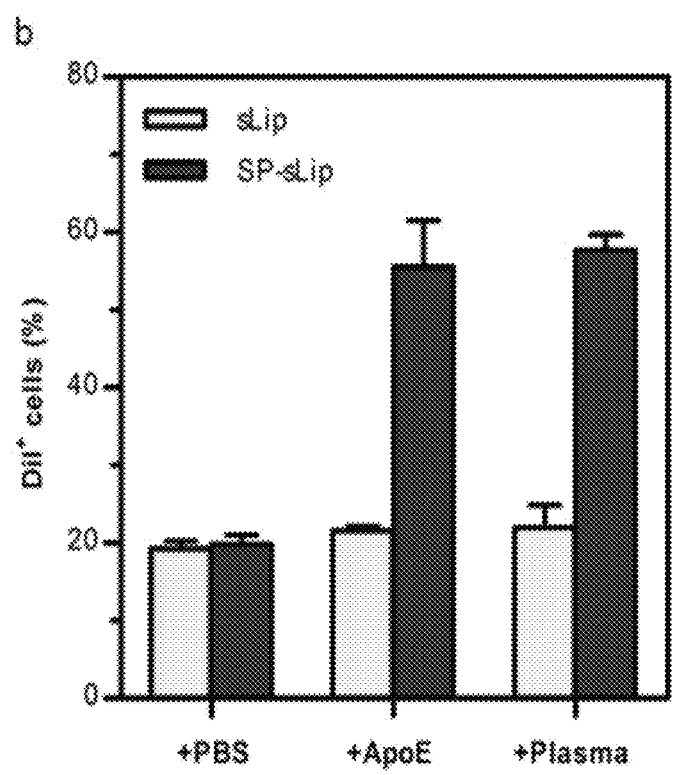

After SP modified liposome (SP-sLip) was incubated with plasma to form protein corona, the uptake of SP-sLip by endothelial cells increased (as shown in FIG. 4A-B).

FIG. 5 is the pharmacokinetic parameters and immunogenicity evaluation of SP modified liposome in mice.

Figure 5A:
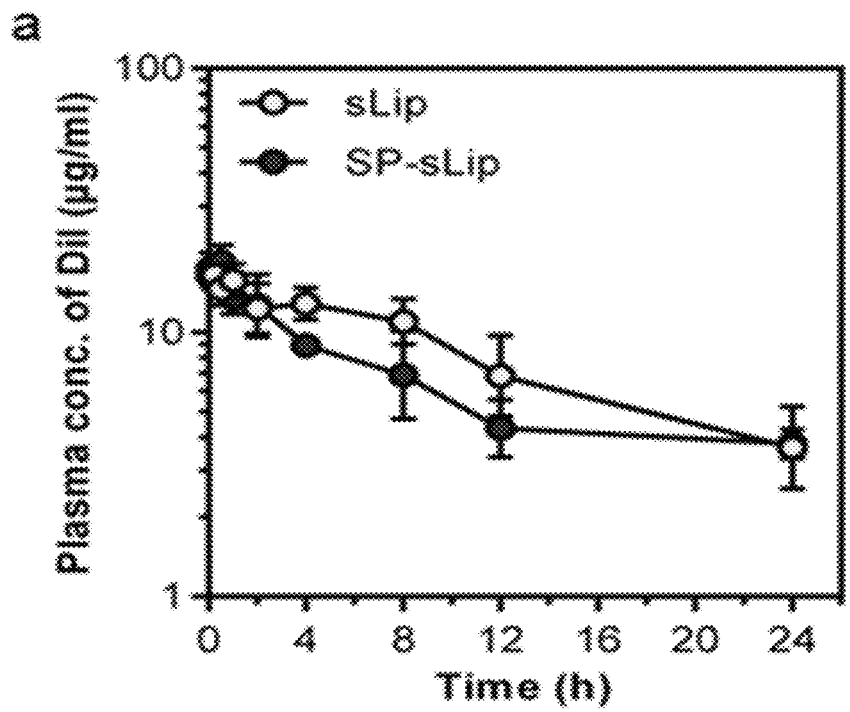
Figure 5B:
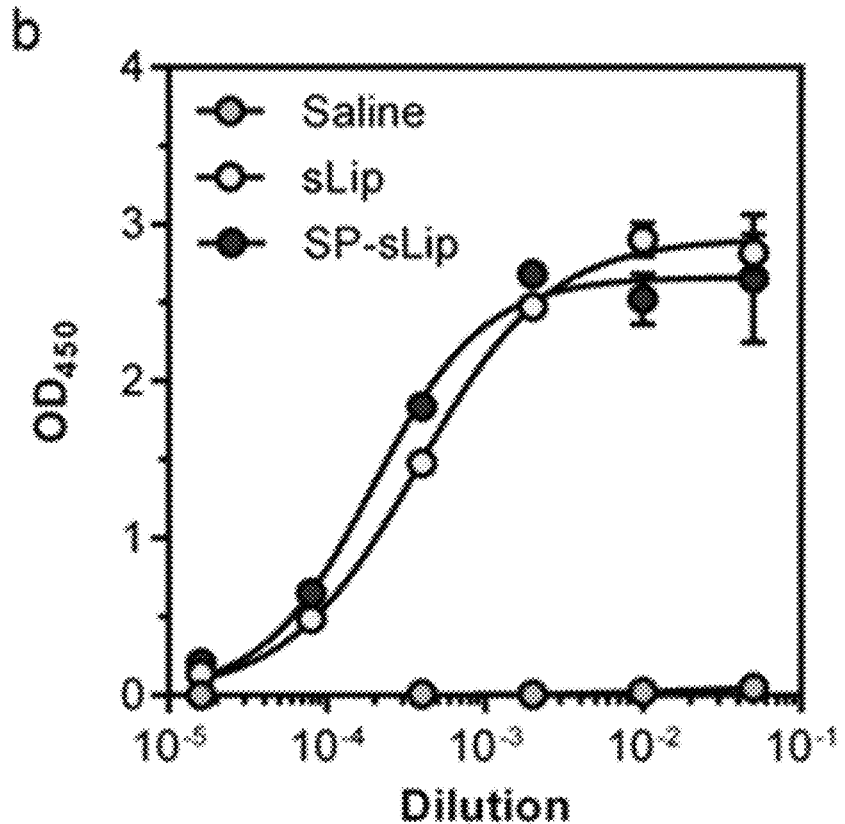
Figures 5C, 5D:
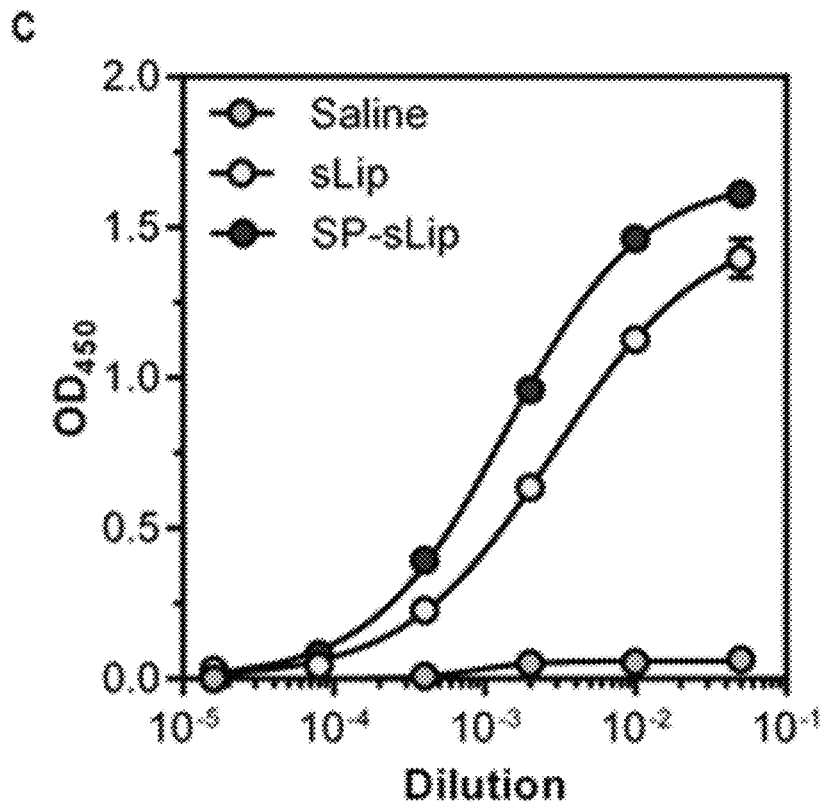

SP was modified on the surface of liposome (SP-sLip), which did not affect the pharmacokinetic parameters of liposome in vivo (as shown in FIG. 5A), and did not increase the immunogenicity of common long-circulating liposomes (taking IgG and IgM in blood as evaluation indexes, as shown in FIG. 5B-D).

Figure 6:
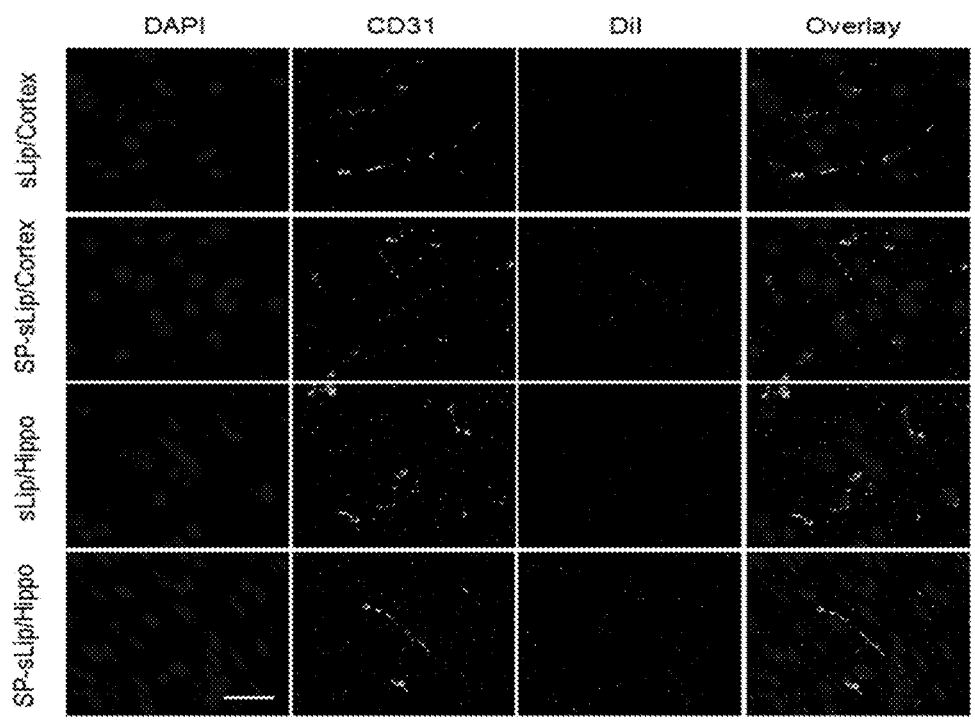

FIG. 6 is the evaluation of brain entry efficiency of SP modified liposomes in mice.

Through in vivo detection of fluorescein in mouse brain, it was found that the amount of cross BBB in SP-sLip group was significantly higher than that in sLip group, which indicated that SP could mediate the delivery system across blood-brain barrier.

Figure 7:
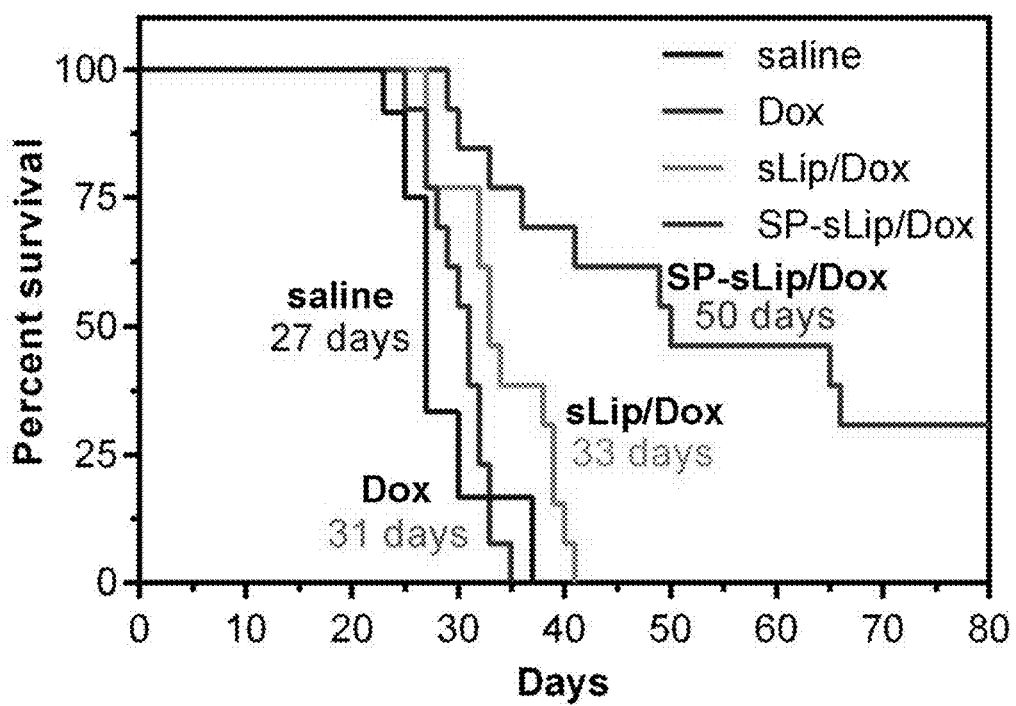

FIG. 7 is the anti-glioma efficacy of adriamycin encapsulated liposomes in vivo.

The median survival time of mice in saline group, DOX group, sLip/DOX group and SP-sLip/DOX group were 27 days, 31 days, 33 days and 50 days, respectively. SP modified liposome could significantly prolong the median survival time of brain orthotopic tumor model mice.

Figure 8:
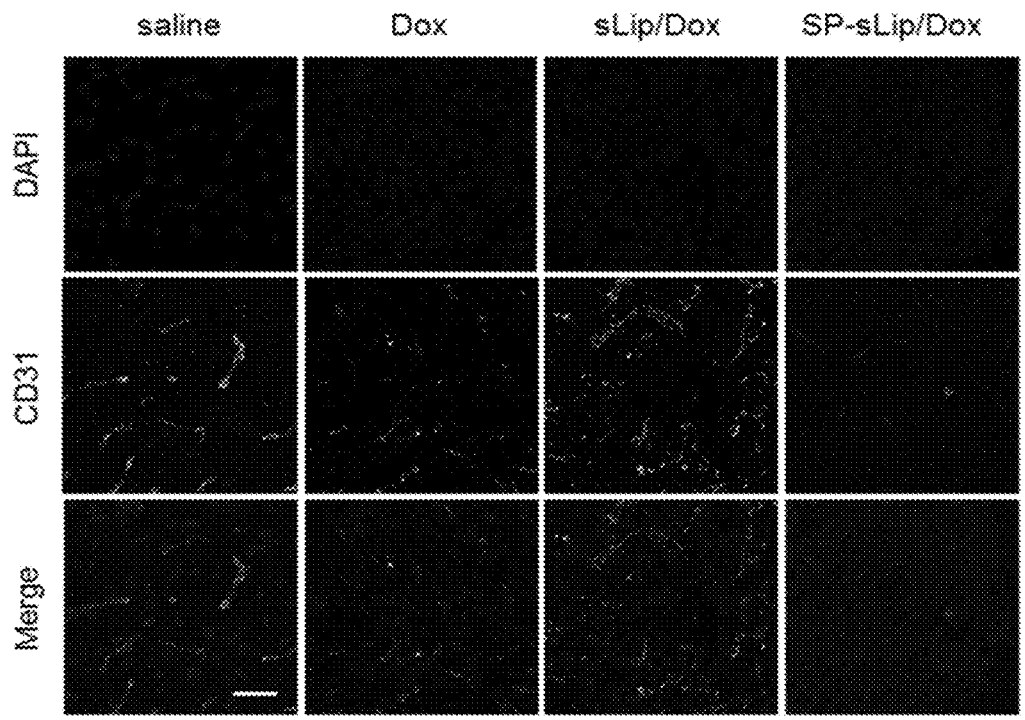

FIG. 8 is the effect of adriamycin encapsulated liposomes on neovascularization in tumor tissue.

The vascular density in tumor tissue of SP modified liposome encapsulating adramycin (SP-sLip/DOX) group was significantly lower than that of unmodified group (sLip/DOX), which indicated that SP could mediate the delivery system to target tumor neovascularization.

Figure 9:
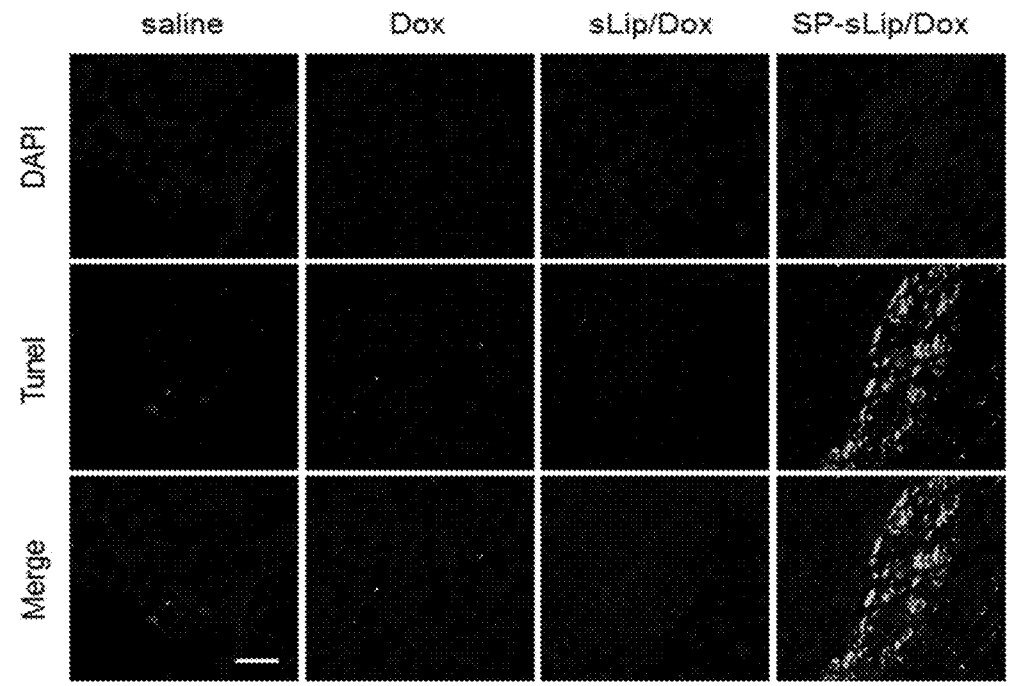

FIG. 9 is the effect of adriamycin loaded liposomes on apoptosis of glioma cells.

The number of apoptosis in tumor tissue of SP modified liposome encapsulating adramycin (SP-sLip/DOX) group was significantly higher than that of unmodified group, which indicated that SP could mediate drug delivery system to target tumor cells.

FIG. 10 is the safety evaluation.

Figure 10A:
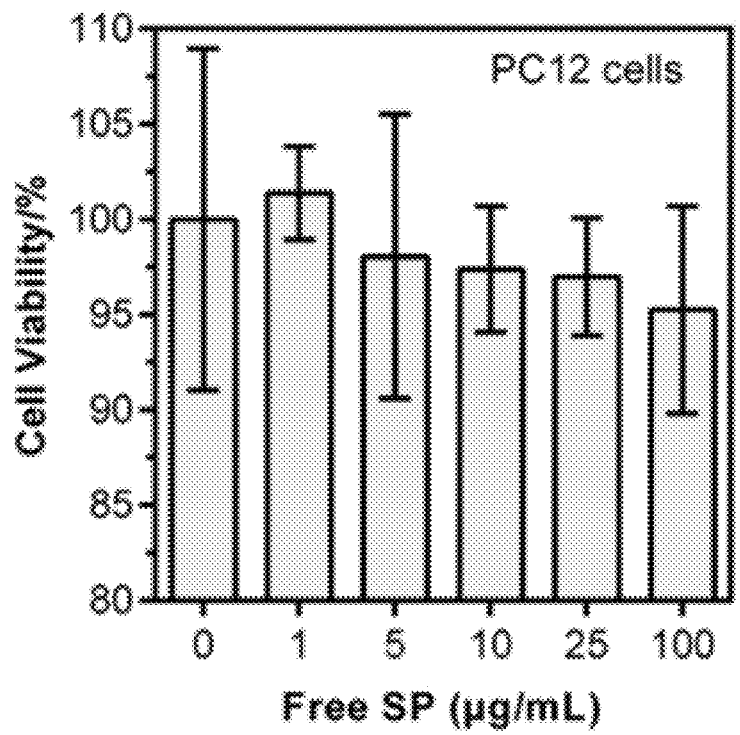
Figure 10B:
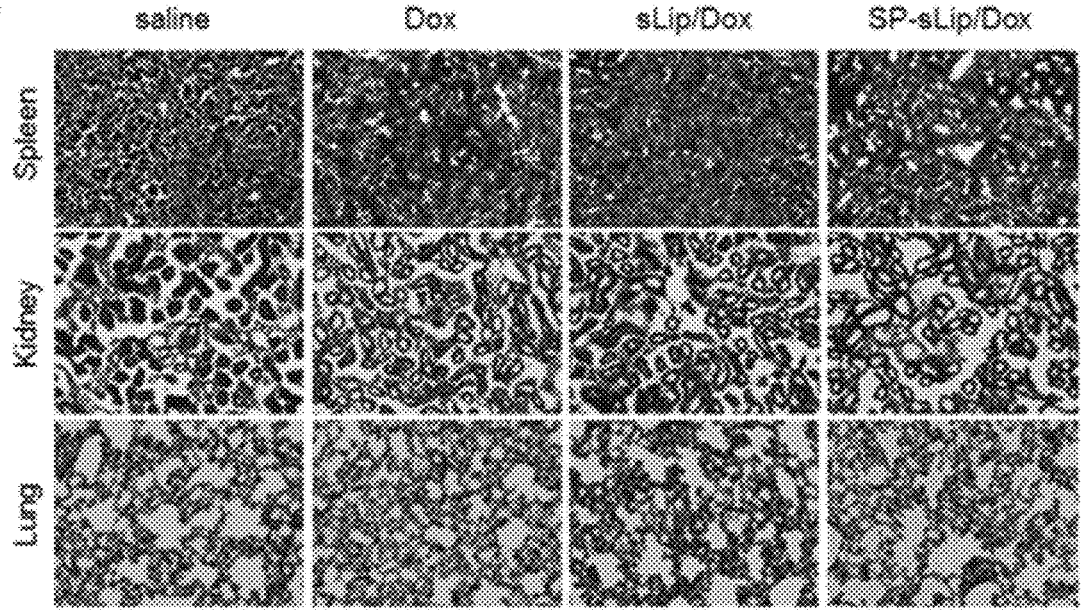

SP did not show cytotoxicity on the neural cell line PC12 cultured in vitro (as shown in FIG. 10A), and there was no obvious abnormality in the tissue sections of mice organs in SP modified liposome encapsulating adramycin (SP-sLip/DOX) group (as shown in FIG. 10B), which indicated that the SP modification did not cause toxic and side effects on the liposome surface.

DETAILED DESCRIPTION OF EMBODIMENTS

The present invention is further illustrated by specific examples below, but it should be understood that these examples are only for more detailed and specific explanation, and should not be understood as limiting the present invention in any form.

This section gives a general description of the materials and test methods used in the test of this invention. Although many materials and operating methods used to achieve the purpose of the present invention are well known in the art, the present invention is described in as much detail as possible here. It is clear to the person skilled in the art that in the context, unless otherwise specified, the materials and operation methods used in the present invention are well known in the art.

Example 1 Preparation of Liposome

Preparation of Liposome sLip/DiI and SP-sLip/DiI:

Preparation of Liposome sLip/DiI: Weigh the membrane material for preparing liposome: natural phospholipid (HSPC): 7.85 mg; cholesterol: 3.35 mg; mPEG-2000-DSPE: 2.78 mg; DiI:0.4 mg, dissolve them in 10 mL CHCl$_3$, suspend in 40° C. water bath to form a film, dry in vacuum to remove organic solvent, dissolve the film in 1 mL double distilled water, shake and hydrate in 60° C. water bath, and extrude in liposome extruder at 400 nm, 200 nm and 100 nm aperture to obtain sLip/DiI.

Preparation of liposome SP-sLip/DiI: Weigh 50 mg Mal-PEG-DSPE, dissolve it in 5 mL CHCl$_3$ at 37° C. to form a film, dry in vacuum for half an hour, dissolve it in 4 mL double distilled water, hydrate at 37° C., and remove large particles by ultrasound. 26 mg SP-Cys protein is weighed and dissolved in 2 mL of double distilled water and mixed with the solution of above membrane material. After washing the container with 1 mL of double distilled water, the mixture was mixed, 40 µL EDTA solution (500 mM, pH 8.0) and 3 mL PB solution (0.1 M, pH 7.4) are added, and stirred at room temperature to react for 6 h, so that there is no flocculent precipitation. Dialysis in distilled water for 48 hours to 72 hours by using dialysis membrane with aperture of 8000-10000 Da, and the freeze-dried product of solution obtained is SP-PEG-DSPE.

Weigh the membrane material for preparing liposome: HSPC: 7.85 mg; cholesterol: 3.35 mg; mPEG-2000-DSPE: 1.67 mg; SP-PEG-DSPE: 1.82 mg; DiI:0.4 mg, dissolve them in 10 mL CHCl$_3$, suspend in 40° C. water bath to form a film, dry in vacuum to remove organic solvent, dissolve the film in 1 mL double distilled water, shake and hydrate in 60° C. water bath, and extrude in liposome extruder at 400 nm, 200 nm and 100 nm aperture to obtain SP-SLIP/DII.

Preparation of Liposome sLip/DOX and SP-sLip/DOX:

Preparation of liposome sLip/DOX: Weigh the membrane material for preparing liposome: HSPC: 7.85 mg; cholesterol: 3.35 mg; MPEG-2000-DSPE: 2.78 mg, dissolve them in 10 mL CHCl$_3$, suspend in 40° C. water bath to form a film, dry in vacuum to remove organic solvent, dissolved in 1 mL ammonium sulfate solution (0.32 M), shake and hydrate in 60° C. water bath, and extruded in liposome extruder with apertures of 400 nm, 200 nm and 100 nm to obtain sLip hydrated by ammonium sulfate solution. After being replaced by physiological saline solvent by G50 elution column, adriamycin aqueous solution is added and mixed (drug-lipid ratio was 1:10), and the uncoated adriamycin is removed by G50 chromatography column to obtain sLip/DOX.

Preparation of liposome SP-sLip/DOX: Weigh the membrane material for preparing liposome: HSPC: 7.85 mg; cholesterol: 3.35 mg; mPEG-2000-DSPE: 1.67 mg; SP-PEG-DSPE: 1.82 mg, other steps are the same as above (preparation of liposome sLip/DOX), so as to obtain SP-sLip/DOX.

Example 2 Binding Activity of Liposome to LRP-1 Receptor after Forming Protein Corona in Serum and the Effect on Uptake by Vascular Endothelial Cells Characteristics of Protein Corona Formed by Liposomes in Serum:

Serum of C57BL/6 mice (containing protease inhibitor and EDTA as anticoagulant) was mixed with liposome at a ratio of 1:1, incubated at 37° C. for 1 h, centrifuged at 15000 rpm for 30 min, washed twice with cold PBS, and dissolved in 30 µL PBS. With serum as positive control and PBS as negative control, 6 µL SDS-PAGE loading buffer and 3 µL β-mercaptoethanol were added, boiled for 10 minutes to denature the protein, separated the proteins with different molecular weights with 4-20% polyacrylamide gel, and color development with rapid silver staining kit. Cut off the obvious difference band (as shown by red arrow) in the PAGE glue and the same position of the control, digested them with trypsin, and resuspended them in 0.1% formic acid solution. Analyzed the protein components of each band by LC-MS/MS, and the experimental results are shown in FIG. 1.

In vivo experiments were carried out as follows: the modified and unmodified liposomes labeled with fluorescent DiI were injected into C57BL/6 mice through tail vein, and the blood was collected after 1 hour and plasma was centrifuged at low speed. The separation method of protein corona was as described in the above in vitro experiment, and the protein corona components adsorbed in vivo were identified by SDS-PAGE and western blot, as shown in FIG. 2.

Binding Activity of SP-sLip and LRP-1 Receptor Before and After Serum Incubation:

ELISA method was used to detect the binding activity between SP-sLip and SP antibody before and after serum incubation, so as to judge the change of active binding domain between SP and receptor after plasma protein interaction, and to detect the activity of apolipoprotein adsorbed by it. The specific operation was as follows: 0.1 µg SP-PEG-DSPE was added to each well of ELISA plate, left overnight at room temperature, washed with PBS for 3 times, sealed with 3% BSA for 1 h, and the BSA solution was sucked off. Added SP antibody, incubated at 37° C. for 1 h, washed with PBS for three times, added liposome incubated with serum or PBS in advance and diluted in gradient, incubated at 37° C. for 1 h, washed with PBS for three times, added corresponding horseradish peroxidase labeled secondary antibody, reacted with TMB chromogenic solution for 3-15 min after 1 h, stopped the reaction with 2 M H$_2$SO$_4$, and measured its absorbance value at 450 nm wavelength. The experimental results are shown in FIG. 3.

Effect of SP-sLip on Uptake by Vascular Endothelial Cells after Forming Protein Corona in Serum:

Resuscitation of vascular endothelial cell bEND3: Thawed freezing bEND3 cells quickly and transferred them to a centrifuge tube pre-filled with culture solution, centrifuged at 1000 r/min for 3 min, discarded the supernatant, added DMEM culture solution containing 10% FBS, gently blew evenly and dropped them into a culture dish, and mixed evenly. The morphology and growth of cells were observed under a microscope and cultured in an incubator at 37° C., 5% CO$_2$ and 95% relative humidity.

Culture of vascular endothelial cells bEND3: Observed the growth of bEND3 cells, i.e. the number, shape and adherence of cells. Drained the old culture solution, add fresh DMEM culture solution containing 10% FBS and mixed evenly, continued to culture in an incubator with 37° C., 5% CO$_2$ and saturated humidity, observed the growth of cells every day, and passaged every 2-3 days, and the cells were in logarithmic growth phase for about 10 days, which can be used for in vitro cell experiments.

Passage of vascular endothelial cells bEND3: Drained the culture solution, washed twice with PBS, added a little 0.25% trypsin, put it in an incubator for 1 min, then added 2-3 mL culture solution to stop digestion, put the cell suspension into several centrifugal tubes in equal parts, centrifuged and discarded the supernatant, added new culture solution and transferred it to a culture dish and put it in an incubator for culture.

Freeze vascular endothelial cells bEND3: After the cell experiment, the cells were frozen for the next use, and the frozen solution (containing 10% DMSO and 90% fetal bovine serum) was prepared in advance and precooled at 4° C. Digested cells with trypsin, added precooled frozen solution, blew gently with dropper and mixed. Added 1 mL cell fluid into each freezing tube, marked the name and date of freezing after sealing, left it at −80° C. overnight, stored it in liquid nitrogen tank and registered for the record.

BEND3 with proper density was inoculated in a 6-well plate and placed in a cell incubator for overnight culture. Fluorescein DiI-labeled liposomes (serum-incubated and serum-non-incubated) were diluted 50 times with DMEM medium without serum, and 1 mL was added to each well to incubate with the cells for 4 h. The culture solution was drained, washed twice with PBS quickly, the cells were digested with trypsin, the digestion was stopped with serum-containing medium, centrifuged and washed again with PBS. Finally, the cells were dispersed in 300 μL PBS, and the percentage of positive cells and fluorescence intensity (excitation wavelength 555 nm, emission wavelength 570 nm) of liposome loaded with DiI were measured by flow cytometry. The experimental results are shown in FIG. 4.

Effect of SP Modification on Pharmacokinetic Parameters and Immunogenicity of Liposomes In Vivo:

SD rats, 3 in each group, were injected sLip/DiI and SP-sLip/DiI through tail vein. Blood was taken from tail (EDTA anticoagulation) before the injection, 5 min, 30 min, 1 h, 2 h, 4 h, 8 h, 12 h and 24 h after the injection, respectively. Supernatant was separated from blood samples, and DiI in plasma was gradiently diluted with normal rat serum. The fluorescence spectrophotometer was used for quantification (excitation wavelength 555 nm, emission wavelength 570 nm), and the experimental results are shown in FIG. 5a. The sLip and SP-sLip loaded with Lipid A were injected intraperitoneally into Balb/c mice once every 7 days, and blood was taken for later use on the 7th day after each injection. ELISA was used to detect the content of IgG and IgM against PEG and SP produced in mice at different time points, and the experimental results are shown in FIG. 5b-c.

Example 3 SP Modified Liposomes can Span BBB

In Vivo Experiments Confirmed that Fluorescein DiI Labeled SP Modified Liposomes (SP-sLip/DiI) can Cross the Blood-Brain Barrier:

The fluorescently labeled SP-sLip/DiI (phospholipid content is 10 mg/mL, DiI content is 0.4 mg/mL) was injected into C57BL/6 mice by tail vein (10 μL/g). After 1 h, the mice were anesthetized with ether, and the brain tissue was taken out, which was fixed in 4% paraformaldehyde for 24 h, dehydrated by 30% sucrose, embedded by OCT, frozen and sectioned. The nucleus were stained by DAPI and the blood vessel was labeled by CD31 antibody, which were observed and photographed under a microscope, and fluorescein DiI labeled methoxy liposome as control, treated by the same procedure, and the experimental results are shown in FIG. 6.

Example 4 Pharmacodynamic Experiment of Adriamycin Encapsulated SP-sLip In Vivo Median Survival Time of Orthotopic Tumor Model Mice:

Establishment of glioma model in nude mice: Took U87 cells in logarithmic growth phase, digested and counted the cells, suspended them with appropriate amount of PBS buffer, inoculated $6\times10^5$ cells (dispersed in 5 μL PBS buffer) to each nude mouse. The nude mice was anesthetized with 7% chloral hydrate before the experiment, fixed with a brain stereotactic instrument, and inoculated the suspended cells to the striatum (i.e. 0.6 mm forward, 1.8 mm to the right, and 3 mm deep of the anterior fontanelle). Regularly observed the state of nude mice after operation.

Nude mice with orthotopic brain tumor model were randomly divided into 4 groups (n=13), and their body weight was recorded on the 7th, 9th, 11th, 13th and 15th day, respectively. 200 μL saline, adriamycin, sLip/DOX and SP-sLip/DOX were injected into tail vein, and the single injection dose of adriamycin was 2 mg/kg, and the survival time of the model nude mice was recorded. The experimental results are shown in FIG. 7.

Inhibitory Effect of Adriamycin Encapsulated SP-sLip on Angiogenesis and Apoptosis of Tumor Cells:

On the 18th day after administration, orthotopic glioma model mice was anesthetized by chloral hydrate, and the brain tissue was separated and fixed with paraformaldehyde, dehydrated and embedded in paraffin. Immunofluorescence staining of CD31 antibody was used to observe and detect the inhibitory effect on neovascularization. Terminal deoxynucleotidyl Transferase-mediated dUTP nick end labeling (TUNEL) was used to detect the apoptosis degree of tumor cells, and confocal fluorescence microscope was used to observe and take pictures. The experimental results are shown in FIGS. 8 and 9.

Safety evaluation: The gradient concentration of SP was co-cultured with nerve cell line PC12 to evaluate its cytotoxicity in vitro. At the same time, the heart, liver, spleen, lung and kidney tissues of mice in the pharmacodynamic test of orthotopic tumor were dissected and fixed in PBS solution of 4% paraformaldehyde, paraffin-embedded sections were made, stained with HE, observed and photographed under a microscope. the experimental results are shown in FIG. 10.

Although the present invention has been described to a certain extent, it is obvious that various conditions can be appropriately changed without departing from the spirit and scope of the present invention. It is to be understood that the present invention is not limited to the described embodiments, but belongs to the scope of the claims, which includes equivalent substitutions of each of the described factors.

The invention claimed is:

1. A method for mediating targeted delivery of a composition to a brain of a subject in need thereof, wherein the composition comprises an amyloid β short peptide (SP) combined with a drug molecule, a diagnostic molecule, a delivery system, or combinations thereof, wherein the SP binds to receptors on blood-brain barrier and crosses the blood-brain barrier, thus mediating targeted delivery of the composition to the brain and can adsorb apolipoprotein in plasma, wherein the method comprises administering the composition to the subject in need thereof;

wherein the amyloid β short peptide consists of the sequence GSNKGAIIGLM (SEQ ID No: 1).

2. The method according to claim 1, wherein the method further comprises diagnosing a brain tumor or a brain disease in the subject, wherein the composition comprises an imaging substance X, wherein the amyloid β short peptide (SP) is linked to the imaging substance X by covalent bond to prepare SP-X, wherein SP-X to image a brain tumor or a diseased brain tissue or cell in the subject.

3. The method according to claim 2, wherein X is a fluorescent molecule selected from a Fluorescein, or a near-infrared dye molecule selected from Sulfo-Cyanine 5 (Cy5), Sulfo-Cyanine 5.5 (Cy5.5), Sulfo-Cyanine 7 (Cy7), New Indocyanine Green (IR820), Indocyanine Green (ICG), 1,1'-dioctadecyl-3,3,3',3'-tetramethylindotricarbocyanine iodide (DiR), 1,1'-Dioctadecyl-3,3,3',3'-tetramethylindodicarbocyanine,4-Chlorobenzenesulfonate Salt (DiD), or 1,1'-dioctadecyl-3,3,3',3'-tetramethylindocarbocyanine perchlorate (DiI).

4. The method according to claim 1, wherein the method further comprises targeted intervention of a brain tumor or a brain disease in the subject, wherein the amyloid β short peptide (SP) is linked to an antitumor drug Y by covalent bond to prepare SP-Y, wherein SP-Y targets the brain tumor or the brain disease.

5. The method according to claim 4, wherein Y comprises gefitinib, icotinib, anlotinib, crizotinib, erlotinib, osimertinib, alectinib, paclitaxel, docetaxel, cabazitaxel, adriamycin, epirubicin, camptothecin, hydroxycamptothecin, 9-nitrocellulose camptothecine or vincristine small molecule antitumor drugs, p53 activating peptide, polypeptide toxin, or polypeptide antitumor drug.

6. The method according to claim 1, wherein the amyloid β short peptide (SP) is linked to polyethylene glycol-Z by covalent bond to prepare SP- polyethylene glycol-Z, wherein SP- polyethylene glycol-Z is used to prepare a nanometer delivery system.

7. The method according to claim 6, wherein (1) Z comprises a phospholipid, a polylactic acid, a lactic-co-glycolic acid or a polycaprolactone; (2) wherein the nanometer delivery system comprises a liposome delivery system, a micelle delivery system, a nano-disc delivery system, a polymer nanoparticle delivery system, or combinations thereof; or both (1) and (2).

8. The method according to claim 7, (a) wherein the SP-polyethylene glycol-phospholipid is used for preparing the liposome delivery system, the micelle delivery system or the nano-disc delivery system; (b) wherein the SP-polyethylene glycol-polylactic acid, the SP-polyethylene glycol-lactic-co-glycolic acid, or the SP-polyethylene glycol-polycaprolactone is used to prepare the micelle delivery system and the polymer nanoparticle delivery system; or both (a) and (b).

9. The method according to claim 8, wherein the method further comprises diagnosing a brain tumor or a brain disease, and wherein the liposome delivery system, the micellar delivery system, the nano-disc delivery system or the polymer nano-particle delivery system is used to encapsulate a diagnostic molecule to trace the brain tumor or the diseased brain tissue or cell.

10. The method according to claim 9, wherein the diagnostic molecule encapsulated in the delivery system comprises 5-carboxyfluorescein 5-FAM, near-infrared dye selected from Sulfo-Cyanine 5 (Cy5), Sulfo-Cyanine 5.5 (Cy5.5), Sulfo-Cyanine 7 (Cy7), New Indocyanine Green (IR820), Indocyanine Green (ICG), 1,1'-dioctadecyl-3,3,3',3'-tetramethylindotricarbocyanine iodide (DiR), 1,1'-Dioctadecyl-3,3,3',3'-tetramethylindodicarbocyanine,4-Chlorobenzenesulfonate Salt (DiD), or 1,1'-dioctadecyl-3,3,3',3'-tetramethylindocarbocyanine perchlorate (DiI).

11. The method according to claim 8, wherein the method further comprises targeting a brain tumor or a diseased brain tissue or cell, wherein the nanoparticle delivery system, the liposome delivery system, the micelle delivery system, the polymer nanoparticle delivery system or the nano-disc delivery system is used for encapsulating an antitumor drug.

12. The method according to claim 11, wherein the antitumor drug encapsulated in the delivery system comprises gefitinib, icotinib, anlotinib, crizotinib, erlotinib, osimertinib, alectinib, paclitaxel, docetaxel, cabazitaxel, adriamycin, epirubicin, camptothecin, hydroxycamptothecin, 9-nitrocellulose camptothecine, vincristine, p53 activating peptide, or polypeptide toxin.

13. The method of claim 1, wherein the subject suffers from a brain metastatic tumor, a primary brain tumor, or both.

* * * * *